USOO5459065A

United States Patent [19]
Aust et al.

[11] Patent Number: 5,459,065
[45] Date of Patent: Oct. 17, 1995

[54] **PROCESS FOR THE DEGRADATION OF COAL TAR AND ITS CONSTITUENTS BY *PHANEROCHAETE CHRYSOSPORIUM***

[75] Inventors: Steven D. Aust, North Logan; John A. Bumpus, Logan, both of Utah

[73] Assignee: Utah State University Foundation, Logan, Utah

[21] Appl. No.: 65,563

[22] Filed: May 21, 1993

Related U.S. Application Data

[63] Continuation of Ser. No. 662,214, Feb. 28, 1992, abandoned, which is a continuation of Ser. No. 183,115, Apr. 19, 1988, abandoned, which is a continuation-in-part of Ser. No. 899,000, Aug. 22, 1986, abandoned, which is a continuation-in-part of Ser. No. 702,944, Feb. 19, 1985, abandoned.

[51] Int. Cl.$^6$ .............................. C07G 1/00; C12N 1/14; C12P 1/02
[52] U.S. Cl. .................. 435/562.5; 135/171; 135/254.1; 210/601; 210/606; 210/610; 210/632
[58] Field of Search ..................................... 435/171, 254, 435/262.5, 254.1; 210/601, 606, 610, 611, 632; 162/1, 9, 72

[56] References Cited

U.S. PATENT DOCUMENTS

| | | | |
|---|---|---|---|
| 3,979,283 | 9/1976 | Prudom | 210/11 |
| 4,478,683 | 10/1984 | Orndorff | 162/161 |
| 4,554,075 | 11/1985 | Chang et al. | 210/611 |
| 4,588,506 | 5/1986 | Raymond et al. | 210/632 |
| 4,623,465 | 11/1986 | Klibanov | 210/632 |
| 4,665,926 | 4/1987 | Chang et al. | 210/611 |

FOREIGN PATENT DOCUMENTS

| | | | |
|---|---|---|---|
| 7068716 | 4/1982 | Japan | 435/256.8 |

OTHER PUBLICATIONS

Webster's 9th New Coll. Dictionary, p. 912, © 1990.

Aust, Steven D. et al. "Application of White Rot Fungus for the In situ Treatment of Oil Contaminated Soil," Proposal of the U.S. Environmental Protection Agency, Application for Federal Assistance (May 28, 1987).

Aust, Steven D., et al., "Application of a White Rot Fungus for the Biodegradation of Coal Tar," Proposal to Department of Energy/Pittsburgh Energy Technology Center (Mar. 11, 1987).

Aust, Steven D., et al. "Biological Hazardous Waste Management," Proposal to the Department of Health and Human Services, Public Health Service Grant Application (Nov. 30, 1987).

Aust, Steven D., et al. "Application of a White Rot Fungus for the Biodegradation of Coal Tar," Proposal submitted to the department of Energy (Jan. 27, 1988).

Aust, et al., "Biodegradation of Halogenated Hydrocarbons," EPA Environmental Research Brief, EPA 600/M–87/012, pp. 1–5 (Jun. 1987).

Aust, Steven, D., et al., "Biodegradation of Environmental Pollutants," Proposal to the U.S. Environmental Protection Agency, Application for Federal Assistance (Feb. 25, 1988).

Bluestone, et al., "Microbes to the Rescue—Hazardous Waste Biotreatment Fights for Recognition," Chemical Week, p. 1–6 (Oct. 29, 1986).

Budiansky, et al., "Toxic Wastes? A Little Fungus May Help," U.S. News & World Report, p. 85 (Nov. 9, 1987).

Bumpus and Aust, "Mineralization of Recalcitrant Environmental Pollutants by a White Hot Fungus," Treatment, pp. 146–151 (1987).

Bumpus, John A., "Biodegradable of Polycyclic Aromatic Hydrocarbons by Phanerochaete Chrysosporium," (1988 manuscript).

Bumpus, John A., et al., "Biodegradation of Organopollutants by a White Fungus in a Bench Scale Wastewater Treatment System," Application for Federal Assistance to the Department of Interior (Jan. 19, 1988).

Bumpus, et al., "Biodegradation of Environmental Pollutants by the White Rot Fungus Phanerochaete Chrysosporium: Involvement on the Lignin Degrading System," Bioessays, vol. 6, No. 4, pp. 166–170 Apr. 27, 1987.

Bumpus, John A., et al., "Biological Oxidations of Organic Compounds by Enzymes from a White Rot Fungus," paper presented to the In Land Disposal, Remedial Action, Incineration and Treatment of Hazardous Waste, Proceedings of the 14th Annual Research Symposium (May 1988).

Bumpus, et al., Science, pp. 1434–1436 (Jun., 1985).

Bumpus, et al., "Biodegradation of Environmental Pollutants by the White Rot Fungus Phanerochaete Chrysosporium," USEPA Eleventh Annual Research Symposium on Toxic Waste Disposal, pp. 120–126 (Apr. 1985).

Bumpus, et al., "Studies on the Biodegradtion of Organopollutants by a White Rot Fungus," International Conference on New Frontiers for Hazardous Waste Management, pp. 404–410 (Sep. 15–18, 1985).

Bumpus, et al., "Biodegradation of DDT [1,1,1–Trichloro–2,2–Bis(4–Chlorophenyl) Ethane] by the White Rot Fungus Phanerochaete Chrysosporium," Applied and Environmental Microbiology, pp. 2001–2008 (Sep. 1987).

Bumpus, et al., "Biodegradation of Organopollutants by Phanerochaete Chrysosporium: Practical Considerations, In: Land Disposal, Remedial Action, Incineration and Treatment of hazardous Waste," Thirteenth Annual Research Symposium, Cincinnati, Ohio, EPA/600/9–87/015, pp. 411–418 (May 1987).

(List continued on next page.)

*Primary Examiner*—Douglas W. Robinson
*Assistant Examiner*—Deborah K. Ware
*Attorney, Agent, or Firm*—Workman, Nydegger & Seeley

[57] ABSTRACT

A method for degrading coal tar, coal tar distillation fractions, and organic compounds specifically those compounds having three or more fused rings, of the type often associated with coal tar, whether derived from coal tar or synthesized independently. According to the present invention degradation takes place by means of the nonspecific degradation reaction used by Phanerochaete chrysoporium to degrade lignin. The degradation reaction occurs in part by means of a lignin degrading enzyme and hydrogen peroxide, both produced by Phanerochaete chrysoporium.

29 Claims, 2 Drawing Sheets

OTHER PUBLICATIONS

Bumpus, John A., et al., "*Biodegradation of Crystal Violet by the White Rot Fungus Phanerochaete Chrysosporium*," Applied and Environmental Microbiology, vol. 54, No. 5, pp. 1143–1150 (May 1988).

Cernaglia, et al., Applied and Environmental Biology, pp. 1070–1075 (May 1982).

Chang, et al., "*Fungal Decolorization of Bleach Plant Effluent*," Recent Advances in Lignin Biodegradation: Proceedings of an International Seminar, pp. 257–268 (May–Jun. 1983).

Chen, C. L., et al., "*Carboxylic Acids Produced Through Oxidative Cleavage of Aromatic Rings During Degradation of Lignin in Spruce Wood by Phanerochaete Chrysosporium*," Chemical Abstracts, vol. 98, No. 16, 18th Apr. 1983, p. 92, No. 127930g; Columbus, Ohio.

Cohen and Gabriele, Applied and Environmental Biology, pp. 23–27 (Jul. 1982).

Eaton, et al., "*Fungal Decolorization of Kraft Bleach Plant Effluent*," vol. 63, No. 10, Tappi (Oct. 1980).

Eaton, D. C., "*Mineralization of Polychlorinated Biphenyls by Phanerochaete Chrysosporium: a Ligninolytic Fungus*," Chemical Abstracts, vol. 103, No. 1, 8th Jul. 1985, p. 169, No. 1754F, Columbus, Ohio.

Faison and Kirk, Applied and Environmental Microbiology, pp. 1140–1145 (Nov. 1983).

Forney, et al., "*The Involvement of Hydrozyl Radical Derived From Hydrogen Peroxide in Lignin Degradation by the White Rot Fungus Phanerochaete Chrysosporium*," the Journal of Biological Chemistry, vol. 257, No. 19, pp. 11455–11462 (Oct. 10, 1982).

Gold, et al., Arch. of Biochem, and Biophysics, vol. 234, No. 2, Nov. 1, pp. 353–362 (1984).

Hatakka, A. L., et al., "*Cultivation of Wood–Rotting Fungi on Agricultural Ligneocelluloic Materials for the Production of Crude Protein*," Chemical Abstracts, vol. 102, No. 19, 13th May 1985, p. 493, No. 165220j, Columbus, Ohio.

Jeffries, et al., "*Nutritional Regulation of Lignin Degradation by Phanerochaete Chrysosporium*," Applied and Environmental Biology, vol. 42, No. 2, pp. 290–296 (1981).

Jong, S. C., Ph.D. and Gantt, M. J., American Type Culture Collection Catalogue of Fungi/Yeasts (1984).

Joyce, T. W., et al., "*A Continuous Biological Process to Decolorize Bleach Plant Effluent*," Biotech. Advs., vol. 2, pp. 301–308, (1984).

Kamaya, Y, et al., "*Degradation of Lignin Substructure Models with Biphenyl Linkage by Phaerochaete Chrysosporium Burds*," Chemical Abstracts, vol. 101, No. 16, 15th Oct. 1984, p. 117, No. 132759t, Columbus, Ohio.

Keyser, et al., "*Ligninolytic Enzyme System of Phanerochaete Chrysosporium: Synthesized in the Absence of Lignin in Response to Nitrogen Starvation*," Journal of Bacteriology, vol., 135, No. 3, pp. 790–797 (Sep. 1978).

Kirk, et al., Applied and Environmental Microbiology, vol. 32, pp. 192–194 (Jul. 1976).

Leatham, et al., "*Degradation of Phenolic Compounds and Ring Cleavage of Catechol by Phanerochaete Chrysosporium*," Applied and Environmetnal Microbiology, vol. 46, No. 1, pp. 191–197 (Jul. 1983).

Lundquist, et al., "*Fungal Degradation of Kraft Lignin and Lignin Sulfonates Prepared from Synthetic 14C–Lignins*," Arch. Microbiol., vol. 112, pp. 291–296 (1977).

Lyr, Nature (Jul. 1962).

Merck & Co., Inc., The Merck Index, p. 345 (1983) § 2371.

Mileski, Gerald J., et al., "*Biodegradation of Pentachlorophenol by the White Rot Fungus Phanerochaete Chrysosporium*," Applied and Environmental Microbiology, vol. 54, No. 9 (Prepublication draft, Sep. 1988).

Remediation Technologies, Inc., "*ReTec and Utah State University to Commercialize White Rot Fungi Technology*," Bulletin No. 4 (Aug. 1988).

Ryan, Timothy P., et al., "*Biodegradation of 2,4, 5–trichlorphenoxyacetic acid in Liquid Culture and in Soil by the White Rot Fungus Phanerochaete Chrysosporium*," paper prepared and submitted to Appl. Microbiol. & Biotechnol. (undated manuscript).

Sundman, et al., "*Fungal Decolorization of Kraft Bleach Plant Effluent–Fate of the Chromphoric Material*," Tappi, vol. 64, No. 9 (Sep. 1981).

Weinstein, et al., Applied and Environmental Microbiology, pp. 535–540 (Mar. 1980).

Zurer, P., "*Fungus Shows Promise in Hazardous Waste Treatment*," Chemical and Engineering News, pp. 17–19 (Sep. 14, 1987).

ns, and aro-
PROCESS FOR THE DEGRADATION OF COAL TAR AND ITS CONSTITUENTS BY *PHANEROCHAETE CHRYSOSPORIUM*

This is a continuation application of Ser. No. 07/662,214 filed Feb. 28, 1992, now abandoned, which is a continuation application of Ser. No. 07/183,115 filed Apr. 19, 1988, now abandoned, which is a continuation-in-part of application Ser. No. 06/899,000 filed Aug. 22, 1986, now abandoned, which is a continuation-in-part of application Ser. No. 06/702,944 filed Feb. 19, 1985, now abandoned.

BACKGROUND

1. Field of the Invention

The present invention is related to methods for degrading certain aromatic pollutants which generally resist degradation in the environment. More particularly, the present invention is related to methods for using white rot fungi, or an enzyme system produced by the fungi, for degrading coal tar, coal tar distillation fractions and constituents, and aromatic organic compounds (particularly polycyclic aromatic compounds) of the type generally found in coal tar or its distillation fractions.

2. Background of the Invention

Disposal of environmental pollutants is of increasing concern in this country and worldwide. Proper disposal is necessary in order to avoid contaminating the environment and poisoning organisms living in a particular environment. In the past, relatively casual disposal procedures have been employed for almost all pollutants. For example, pollutants were often simply dumped into a river, ocean, or other body of water. When water was not available, pollutants were often buried or spread across an area of land. While disposal procedures have improved dramatically, generally in response to increased environmental regulation, the effects of failing to properly dispose of pollutants in the past still persists.

Some pollutants are not easily degraded in the natural environment. As a result, these persistent pollutants may be found at disposal sites years, and even decades, after disposal. These pollutants continue to threaten the environment and individuals living in the environment until the pollutants are finally removed or degraded by extraordinary means.

Some of the most persistent and toxic environmental pollutants comprise cyclic organic molecules; large quantities of which have been disposed of improperly. Chemical manufacturing plants and industrial sites using such chemicals are some of the major sources of these chemicals.

One major source of cyclic organic molecules is coal tar and related compounds. Cyclic organic compounds are often found as constituents of coal tar. The present invention relates to methods for degrading coal tar, coal tar distillation fractions, and cyclic organic molecules of the type generally found in coal tar, whether derived from coal tar or another independent source.

In the past, coal tar and related materials have been produced widely and in large quantities. Unfortunately, disposal methods have been extremely casual and inadequate.

One major source of pollution by coal tar and coal tar related organic compounds was the gasification of coal and oil prior to the widespread use of natural gas. Coal and oil gasification processes produced coal tar and coal tar related compounds in great abundance. As a result, almost every utility operating during the period of time in which coal and oil was commonly gasified has an associated disposal site. It is currently estimated that there are over 2,000 major coal tar disposal sites in the United States alone.

Coal tar and related aromatic organic compounds are also widely used in industry, including the utility and railroad industries. One use of coal tar and coal tar distillation fractions is in treating wood for use as railroad ties and utility poles. This treatment prevents degradation of the wood while it is exposed to the environment. The very features of coal tar and coal tar distillation fractions which make them usable as wood preservatives, however, also make them difficult to dispose of in the environment.

Many of the component molecules of coal tar are not easily degraded by microorganisms found in nature. Coal tar consists of numerous different components. One of the commonly used distillation fractions of coal tar is creosote. Another distillation fraction of creosote is anthracene oil. The present invention is directed to a process for degradation of coal tar distillation fractions of this type, as well as coal tar itself.

Coal tar also contains several different aromatic organic molecules. These range from single ring compounds such as p-cresol, to multiple ring compounds such as benzo(a)pyrene. Intermediate cyclic organic molecules are also commonly found in coal tar. For example, naphthalene and 2-methylnaphthalene are constituents of coal tar. Degradation of all of the above classes of organic molecules, whether derived from coal tar or from another source, fall within the scope of the present invention.

As mentioned above, aromatic hydrocarbons are difficult to degrade in nature. Most microorganisms are unable to significantly degrade many of these molecules, particularly the more complex multiple ring aromatics. Polycyclic aromatics are, therefore, persistent organic pollutants for which those skilled in the art have long sought to develop adequate and safe methods of disposal. Once these compounds have been disposed of in the environment, they break down only slowly, if at all. Thus, large quantities of these compounds disposed of forty (40) to fifty (50) years ago may still yet be found today at a disposal site.

A serious related environmental problem is that some of these compounds, particularly lighter aromatic hydrocarbons, are at least somewhat water soluble. For example, p-cresol is known to be relatively water soluble. Double ring compounds such as 2-methylnaphthalene are also found to be at least somewhat water soluble. Accordingly, these compounds present a serious threat to ground water. Water flowing through a disposal site will leach some of the soluble hydrocarbons from out of the site. These hydrocarbons can then be introduced into the general ground water.

As mentioned above, most microorganisms are not able to cause complete biodegradation of polycyclic aromatic compounds. A few species of bacteria and fungi are able to cause degradation of relatively simple aromatics. However, polycyclic aromatic compounds, such as benzo(a)pyrene, are generally very resistant to biodegradation.

Although some microorganisms have been found which are able to degrade certain polycyclic aromatic compounds, their usefulness in microbial waste systems is often limited. Degradation using these species is not generally extensive and does not usually proceed to degrade the polycyclic aromatic compounds to carbon dioxide and water as end products of metabolism. Unfortunately, some metabolites of degradation may be more toxic than the parent compound and these intermediates may also be environmentally persistent. Thus, incomplete degradation can create a situation which is worse than the original problem.

Microorganisms conventionally used in waste treatment systems are generally selective in the compounds they act upon and are not able to degrade a wide variety of organo-pollutants. Thus, mixtures of pollutants are not totally biodegradable using the processes of the prior art. Attempts have been made to degrade such mixtures with mixtures of microorganisms. This type of system has, however, met with limited success and is extremely complex in its application.

It would, therefore, be a major advancement in the art to provide a process for the degradation of coal tar, distillation fractions and constituents of coal tar, and compounds often associated with coal tar including cyclic and polycyclic aromatic compounds. It would be a related advancement in the art if such a process could be used directly in the environment such that coal tar disposal sites could be treated in situ. It would be a further advancement in the art to provide simple, yet economical methods for the degradation of these compounds.

It would also be an advancement in the art to provide methods which were thoroughly effective and which left no toxic intermediates in the degradation process. Similarly, it would be an advancement in the art to provide a process for thoroughly degrading coal tar, its constituents, and related pollutants using a single microorganism.

Such methods are disclosed and claimed herein.

BRIEF SUMMARY AND OBJECTS OF THE INVENTION

The present invention is related to methods for degrading coal tar, coal tar distillation fractions and constituents, cyclic aromatics, and particularly polycyclic aromatic compounds. According to the present invention, degradation may take place in situ, such as at a coal tar disposal site. Alternatively, the degradation may take place in a reaction vessel partially or totally isolated from the surrounding environment.

The present invention teaches the degradation of the organic pollutants using a white rot fungus. Any genus or species of white rot fungus is acceptable and usable within the scope of the present invention, providing it possesses the characteristics described in greater detail hereinafter. It will be appreciated that experimentation and examples contained herein emphasize the use of the widely accepted standard white rot fungus, *Phanerochaete chrysosporium*. The present invention is not, however, intended to be limited to the application and use of this particular genus and species of fungi.

It has been found that white rot fungi are capable of degrading lignin. Indeed, for the purposes of the present invention, one definition of the term "white rot fungus" is a fungus that is capable of degrading aromatic carbon atoms in lignin to carbon dioxide.

Lignin is a naturally occurring, highly complex, nonrepeating heteropolymer that provides structural support in woody plants. Like many synthetic organic molecules, lignin is resistant to attack by most microorganisms. Indeed, lignin biodegradation is generally thought by those skilled in the art to be the rate limiting step in the carbon cycle.

It has been found, however, that white rot fungi are able to degrade lignin. Because of the ability of white rot fungi to generate carbon-centered free radicals, the enzyme system of white rot fungus is able to catalyze numerous, nonspecific cleavage reactions in the lignin "lattice." The resultant heterogenous mixture of low molecular weight aromatic compounds may then undergo further modification or aromatic ring cleavage and metabolism to carbon dioxide by more conventional enzyme systems.

In a similar manner, it has been found that the white rot fungi degrade coal tar, coal tar distillation fractions and constituents, and cyclic and polycyclic aromatic compounds which are often associated with coal tar. These materials are degraded using the nonspecific, lignin-degrading enzyme system of white rot fungi. This nonspecific degradation process is used to degrade these organic pollutants to a nontoxic end product. For example, it may be desirable to degrade the organic compound to the point where only carbon dioxide and water remain. Alternatively, the reaction may be stopped at any point where only desirable degradation intermediates remain. It will be appreciated that, given time, the process of the present invention would generally continue degradation to carbon dioxide and water.

During the degradation process, it has been found that the white rot fungi produce hydrogen peroxide, as well as the degradation enzymes. Hydrogen peroxide is known to facilitate degradation in connection with the enzyme system produced. Thus, it is one teaching of the present invention that degradation preferably occurs in the presence of hydrogen peroxide, whether added to the system or produced within the system by the white rot fungi.

Likewise, degradation occurs best under aerobic conditions. Accordingly, the present invention teaches the preferred use of aerobic conditions in order to degrade the organic pollutants most efficiently and quickly.

The present invention teaches mixing of coal tar, or cyclic or polycyclic aromatic constituents or fractions of coal tar, with white rot fungus and appropriate nutrients under aerobic conditions. The mixture may also be supplemented at any time as desired by providing additional lignin degrading enzymes and hydrogen peroxide.

The invention is specifically directed to the degradation of hard-to-degrade polycyclic aromatic compounds. At the same time, easier to degrade organo-pollutants, such as single ring aromatic compounds, will also be degraded by the white rot fungi, when used according to the methods of the present invention.

It has been found in experiments that degradation through the use of white rot fungi may slow at certain points in the reaction. White rot fungi, however, can again be activated by adding nutrients; glucose has been found to be a suitable nutrient.

Accordingly, it is a primary object of the present invention to provide methods for degrading coal tar, coal tar distillation fractions and constituents, and polycyclic aromatic organic compounds of the type often associated with coal tar, whether produced from coal tar or synthesized independently.

It is a related object of the present invention to provide a process for degrading such pollutants directly in the environment without the use of expensive collection and transportation procedures.

It is a further object of the present invention to provide simple and economical methods of degrading organic pollutants of the type described herein.

It is also an object of the present invention to provide a process for degrading persistent organic pollutants, which process is thoroughly effective and does not produce toxic intermediates or reaction products.

It is also an object of the present invention to provide such a process which uses only a single microorganism or a single class of microorganisms (i.e., white rot fungi).

These and other objects of the invention will become apparent upon reading the following detailed description and appended claims, and upon reference to the accompanying drawings.

DETAILED DESCRIPTION OF THE PREFERRED EMBODIMENTS

Figure 1:
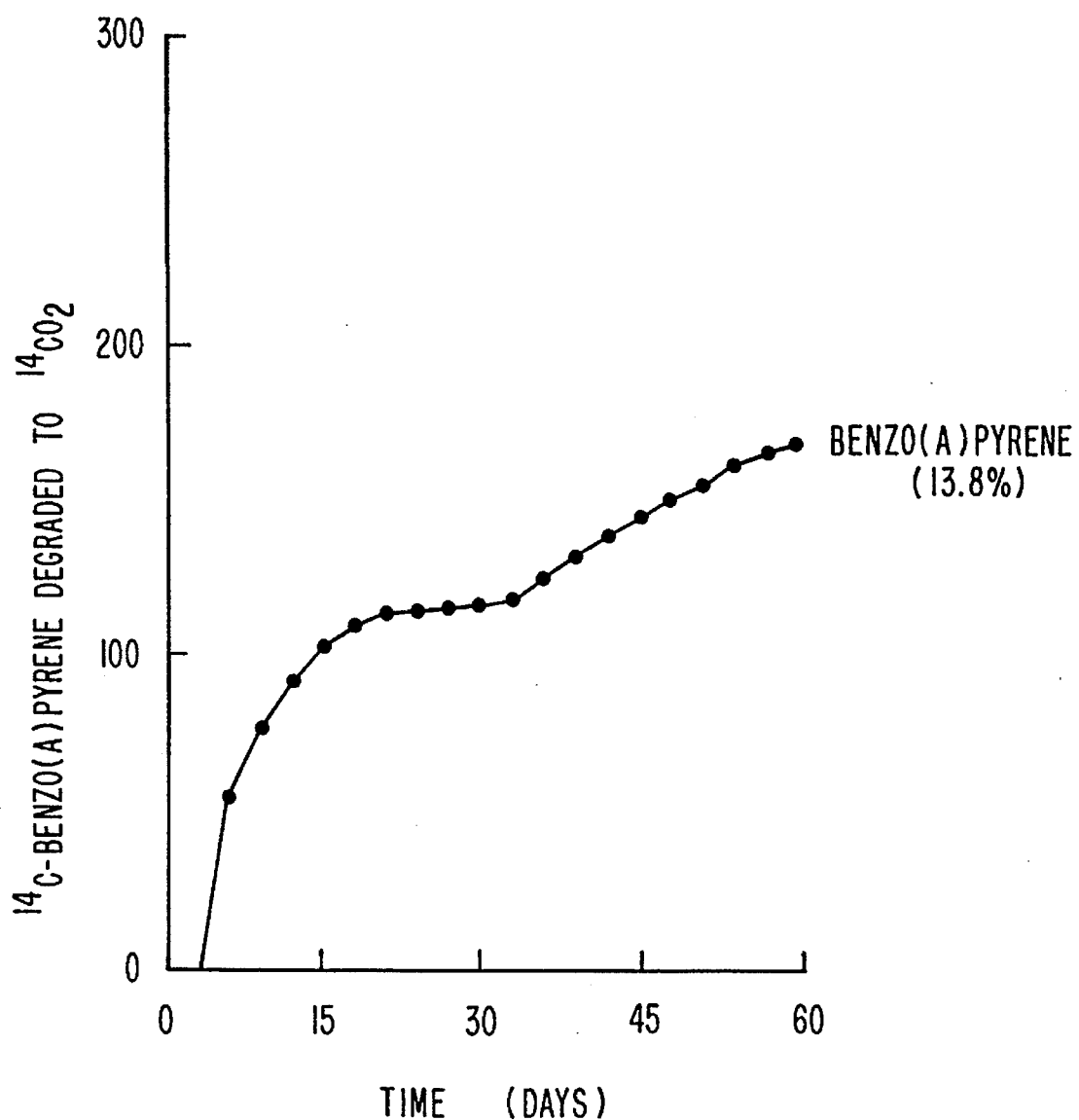
FIG. 1 is a graph illustrating degradation of benzo(a)pyrene by *Phanerochaete chrysosporium*.

The present invention is directed to a process for degrading organopollutant compounds, such as those comprising coal tar and coal tar distillation fractions and constituents. The presently preferred embodiment of the process of the present invention comprises reacting an organopollutant compound which persists in the environment with fungal enzymes containing a lignin-degrading peroxidase, in the presence of hydrogen peroxide. The reaction preferably takes place under aerobic conditions. The reaction is allowed to continue until the persistent organopollutant has been degraded to a nontoxic compound or to carbon dioxide and water as may be desired.

It will be appreciated that the present invention may take place in an aqueous medium or by mixing the fungus directly with the pollutants. According to the present invention, the enzyme and hydrogen peroxide may be added directly to the pollution source, or alternatively, the fungus (which will produce the enzyme and hydrogen peroxide) may be simply added to the pollution source. While one alternative or the other may be more efficient or effective under given conditions, either procedure will work for most coal tar pollution sources.

According to the latter embodiment, the present invention relates to a process where the lignin-degrading enzymes and hydrogen peroxide are provided by a biologically pure culture of lignin-degrading fungus or a mixture of lignin-degrading fungi. By adding the fungus directly, the need to introduce the hydrogen peroxide and enzymes periodically into the reaction mixture is avoided because the fungus itself produces both the extracellular enzyme and the hydrogen peroxide.

Many fungi of the class *basidimycetes* are collectively known as white rot fungi and are ubiquitous in nature. Hence these fungi can be released in concentrated form in soil or wastes containing the pollutant organic compounds since no new organisms representing a potential danger to the environment are used.

All fungi which produce lignin degrading enzymes fall within the scope of the present invention and are defined herein collectively as "white rot fungi." Any fungus which is capable of degrading lignin in the manner described herein is to be considered within the scope of the present invention.

*Phanerochaete chrysosporium* is the experimentally accepted standard and, accordingly, the data presented herein was produced using that particular fungus. *Phanerochaete chrysosporium* is known to produce lignin-degrading peroxidases having molecular weight of approximately 38,000–45,000 daltons.

The present invention also includes processes for controlling the degradation process and even stopping the degradation process at any point that is desirable. For example, it may be desirable under certain circumstances to terminate the degradation reaction when a nontoxic intermediate is present, rather than allowing complete degradation of the pollutant. This is particularly useful when the process is used in a reaction vessel, rather than in situ.

The present invention also teaches the addition of nutrients to the white rot fungus during the process in order to maintain efficient and effective degradation. It is often found that the degradation process may slow after a period of time while the addition of glucose will reinitiate the degradation process. It may be desirable to add a nutrient to the system for which the white rot fungus will not face extensive competition from other microorganisms.

Accordingly, a lignin-containing nutrient is often preferred since competing microorganisms are often unable to degrade the lignocellulosic material and thus deprive the white rot fungus of the nutrient. Suitable examples of lignin-containing nutrients include corn cobs, sawdust, and straw. Hence, these inexpensive nutrients can be periodically added to the pollution site to assure continuing degradation.

When it is desirable to add the fungus directly to the pollutant, it may also be desirable to provide an associated nutrient. Accordingly, in one preferred embodiment of the present invention the fungus is mixed with the persistent organopollutant along with water and corn cobs, wheat straw, peanut shells, sawdust, or peas.

The mixture of the fungus, water, nutrient, and pollutant is allowed to degrade the pollutant under aerobic conditions using the lignin-degrading system of the fungus. At the appropriate time, the reaction may be stopped by adding an organic solvent to terminate the reaction, thereby leaving a desirable intermediate product. Alternatively, degradation may be allowed to proceed until the pollutant has been essentially completely converted to carbon dioxide and water.

As mentioned above, the peroxidases (enzymes) from the white rot fungus can be used directly for the reaction with the coal tar pollutant. Alternatively the peroxidases can be obtained in a purified form by taking a culture filtrate from the fungi, dialyzing the liltrate, and lyophilizing the dialyzate to prepare a concentrate of the enzyme. The peroxidases and the hydrogen peroxide are then reacted with the pollutant organic compound in aqueous solution or in suspension. The hydrogen peroxide can be either directly provided or generated in situ using an $H_2O_2$ generating enzyme such as glucose and glucose oxidase.

The fungus is preferably grown in a low nutrient nitrogen-containing growth medium. Such an environment has been found to stimulate ligninolytic activity. The cultures are preferably grown at a temperature in the range of from approximately 37° C. to approximately 39° C. for about six days. A source of carbon, nitrogen, minerals, and the vitamin thiamine are also preferably added to the system.

The pollutant organic compounds treated by the present invention can be mixed with various aerobic matrices using a small volume of acetone which may then be allowed to evaporate. These matrices may include lignin, cellulose, wood shavings, sawdust, or humus. Water is added to the matrix to the amount of about fifty percent (50%) by weight moisture. The fungus is then added and incubation occurs at approximately 39° C. in air or oxygen.

It is notable that the pollutant degradation system of the present invention is not induced by the presence of the pollutant substrate. Nitrogen deficiency produces the secondary metabolism which causes production of the enzyme system necessary to degrade the organic pollutants. Thus, high levels of the substrate (the coal tar constituent or the like) are not required in order to initiate degradation.

Degradative enzymes are secreted and appear to have no adverse affect on the fungus. The result is that the initial reactions of coat tar or coal tar degradation are extracellular.

Since the enzyme system secreted by the fungus has a broad specificity, the process of the present invention can be used to degrade complex mixtures of organic compounds such as coal tar, creosote, and anthracene oil. The process is particularly advantageous for certain creosote-containing mixtures containing pentachlorophenol since pentachlorophenol undergoes dehalogenation and degradation to $CO_2$ by these fungi.

The fungus may also be packaged for shipment and use in a manner so as not to activate the fungus. Generally, this is accomplished using dry or anaerobic packaging conditions known in the art.

In summary, the present invention provides for degrading numerous types of persistent organic pollutants such as coal tar, coal tar distillation fractions and constituents, cyclic aromatics, and particularly polycyclic aromatic compounds. The nonspecific lignin-degrading system of the white rot fungus is found to be an efficient means for degrading numerous different pollutant molecules.

EXAMPLES

The following examples are illustrative of the process of the present invention, but are not intended to limit the scope of the present invention.

Example 1

In this example benzo(a)pyrene was degraded using cultures of *Phanerochaete chrysosporium*. Benzo(a)pyrene is a polycyclic (five ring) aromatic compound found in coal tar, and is also representative of a carcinogenic coal tar component. Benzo(a)pyrene is very difficult to degrade in the environment.

Benzo(a)pyrene was $^{14}C$-labeled. The compound was then degraded in a culture of *Phanerochaete chrysosporium*. Degradation, as assayed by $^{14}CO_2$ evolution, was monitored for 30 days at which time supplemental glucose was added and degradation was monitored for another 30 days. Thus a total 60-day degradation period was employed.

The compound was incubated in aqueous cultures as described in U.S. patent application Ser. No. 702,944 filed Feb. 19, 1985, entitled "Process For The Degradation Of Environmentally Persistent Organic Compounds" to Bumpus et al. The culture medium was nutrient nitrogen deficient and was composed of 56mM glucose, 1.2mM ammonium tartrate, and 20mM dimethyl succinate buffer (pH 4.2 to 4.3). Ten milliliter cultures also contained trace amounts of thiamine and minerals as described by Kirk et al., Archives of Microbiology 117:277–285 (1978) (hereinafter referred to as "Kirk"). The initial concentration of $^{14}C$-benzo(a)pyrene was 1.25 moles per culture. Evolution of $^{14}CO_2$ from benzo(a)pyrene was monitored as described by Kirk.

All cultures were equipped for $^{14}CO_2$ evolution studies as described by Kirk.

All cultures were incubated at 37°–39° C. for 3 days under ambient atmosphere. At day 3, the first time points were taken by flushing with 99.7% $O_2$ as described by Kirk. Subsequent time points were taken at three (3) day intervals.

The results obtained in this example clearly indicate that benzo(a)pyrene is degraded to $CO_2$ by the enzyme system of *Phanerochaete chrysosporium*. FIG. 1 shows the results for the degradation of benzo(a)pyrene with *Phanerochaete chrysosporium*. As can be seen, this resistant chemical is degraded to $CO_2$.

It will be appreciated that the culture medium can be supplemented with more nutrient medium including particularly an additional carbon source and the process reinitiated until degradation is complete. The carbon source can be glucose, cellulose or any other compound which provides energy to the white rot fungus.

Example 2

In this example, p-cresol was degraded by *Phanerochaete chrysosporium*. P-cresol is a monocyclic aromatic and is found in abundance in coal tar. P-cresol is relatively water soluble and presents a major threat to ground water.

In this example, p-cresol is degraded according to the method described in Example 1. The initial concentration of p-cresol was 5 nmoles/per culture.

Following this procedure, it was found that p-cresol was degraded to $CO_2$. The results are graphically illustrated in FIG. 2.

This example clearly illustrates the ability of white rot fungus to degrade p-cresol, a coal tar constituent.

Example 3

In this example 2-methylnapthalene was degraded by *Phanerochaete chrysosporium* according to the same methods described in Example 2. 2-methylnapthalene is found abundantly in coal tar. 2-methylnapthalene is found to be slightly water soluble and, therefore, a threat to ground water. This compound is representative of two ring polycyclic compounds found in coal tar.

Degradation took place according to the method described in Example 1. The initial concentration of 2-methylnapthalene was 5 nmoles/per culture.

Figure 2:
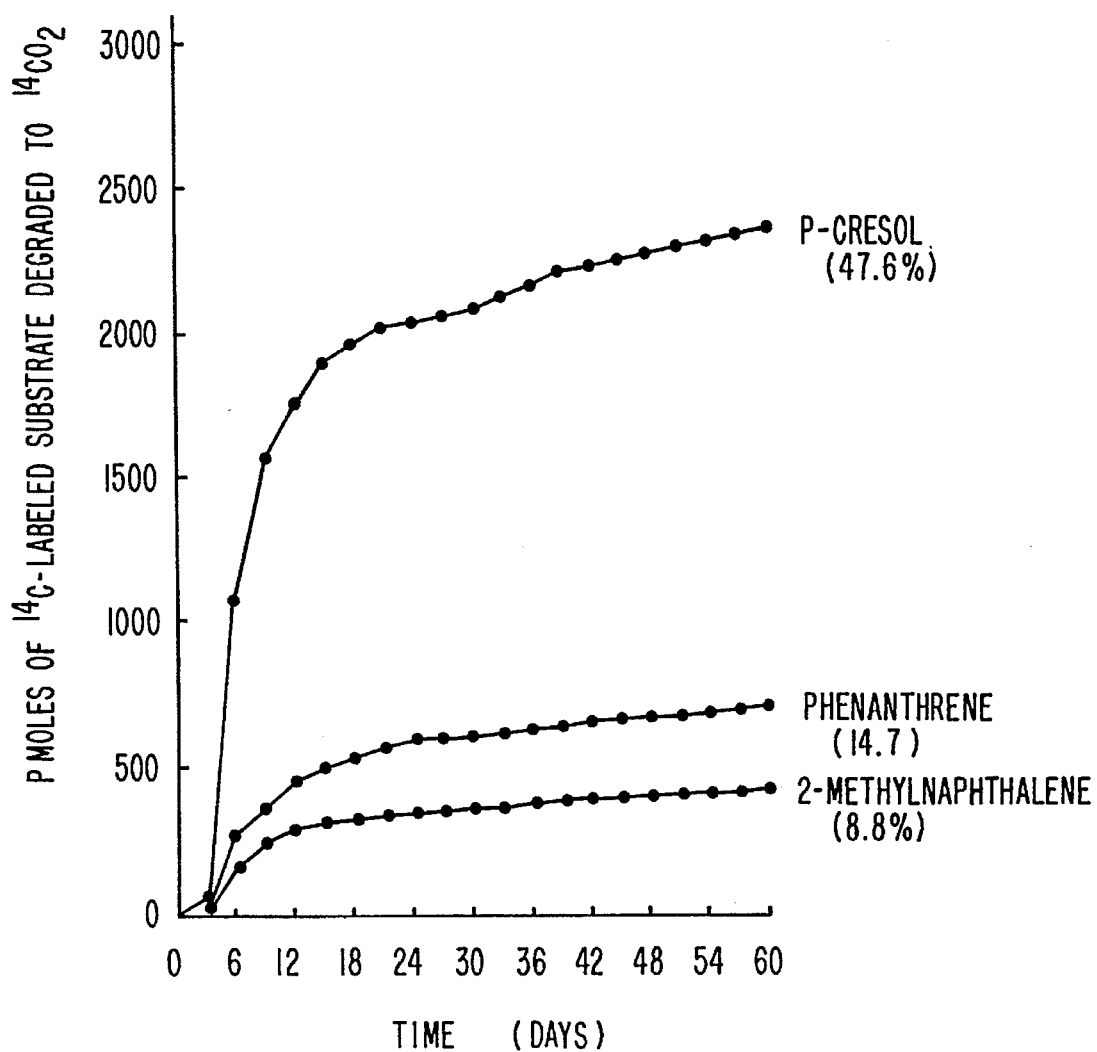
FIG. 2 is a graph illustrating degradation of p-cresol, phenanthrene, and 2-methylnaphthalene by *Phanerochaete chrysosporium*.

Significant degradation occurred, and the results are graphically illustrated in FIG. 2. This example clearly illustrates the ability of white rot fungi to degrade 2-methylnapthalene, a coal tar constituent.

Example 4

In this example phenanthrene was degraded according to the methods set forth in Example 1. Phenanthrene is a polycyclic compound found in coal tar and is a suspected carcinogenic compounds. Phenanthrene is a three ring compound and is representative of three ring compounds found in coal tar.

Degradation took place according to the method described in Example 1. The initial concentration of phenanthrene was 5 nmoles/culture.

Significant degradation occurred and the results are graphically illustrated in FIG. 2.

This example clearly illustrates the ability of white rot fungi to degrade phenanthrene, a coal tar constituent.

Example 5

In this example, a culture of *Phanerochaete chrysosporium* is prepared according to the teachings of this application. The white rot fungus is kept in an aqueous environment which includes corn cobs. The mixture of water, fungi and corn cobs is stored in five gallon drums. Five gallon drums of the white rot fungi/corn cob mixture are transported to a site containing coal tar pollution. The white rot fungi mixture is combined with the contaminated soil and degradation of coal tar components in the soil is observed. Following an approximate 30-day period, additional corn cobs are added to the soil and degradation of coal tar components again continues.

The results of this treatment is that toxic coal tar components in a contaminated soil site are degraded to nontoxic degradation products, including specifically carbon dioxide and water.

Example 6

In this example, anthracene oil found in anthracene oil polluted soil is degraded according to the methods set forth in Example 5.

It is found that significant degradation of the toxic components of anthracene oil takes place in the soil containing the white rot fungus mixture.

Example 7

In this example, creosote found in creosote polluted soil is degraded according to the methods set forth in Example 5.

It is found that significant degradation of the toxic components of creosote takes place in the soil containing the white rot fungus mixture.

During the first 3 days of incubation, cultures were allowed to grow under an atmosphere of air in culture bottles equipped with a gas exchange manifold. After 3 days, and at 3-day intervals thereafter, cultures were gently flushed with oxygen. The atmosphere from each culture was forced through 10 ml of an ethanolamine-containing scintillation cocktail which served as a $CO_2$ trap. Radioactivity in the $CO_2$ was assayed by liquid scintillation spectrometry.

Table 1 below shows that a variety of polycyclic aromatic hydrocarbons are mineralized by *Phanerochaete chrysosporium* under nutrient nitrogen-limiting conditions. In general, very little or no mineralization occurred during the first 3 days of incubation in spite of the fact that abundant growth, as evidenced by the appearance of a mycelial mat, occurred during this time. However, substantial mineralization typically began between day 3 and day 6 of the incubation and usually was maximal between day 3 and days 12 to 18. Although the rate of mineralization generally declined during the last one-half of the 30-day incubation period, in no case did mineralization cease. Furthermore, when supplemental glucose was added after 30 days of incubation, the rate of mineralization of $^{14}C$-labeled compounds increased in all cases.

TABLE 1

| | Initial Concentration of $^{14}C$-labeled Compound | Radiolabeled Substrate Evolved as $^{14}CO_2$ (pmoles) | | % of Radiolabeled Substrates Evolved as |
|---|---|---|---|---|
| | (nmoles/culture) | 30 days | 60 days | $^{14}CO_2$ in 60 Days |
| Phenanthrene | 5.0 | 621.0 | 738.4 | 14.8 |
| 2-methylnapthalene | 5.0 | 366.1 | 436.6 | 8.7 |
| P-cresol | 5.0 | 2086.8 | 2378.1 | 47.6 |
| Biphenyl | 1.25 | 366.8 | 455.8 | 36.5 |
| Benzo[a]pyrene | 1.25 | 117.2 | 171.9 | 13.8 |

Example 8

*Phanerochaete chrysosporium* (BKM-F-1767) was obtained from the United States Department of Agriculture, Forest Products Laboratory, Madison, Wis. The fungus was maintained on malt agar slants at room temperature until used. Subcultures were routinely made every 30–60 days.

Carbon-14 labeled phenanthrene (10 mCi/mmole), 2-methylnapthalene (8.57 mCi/mmole), p-cresol (10.33 mCi/mmole), and biphenyl (15.91 mCi/mmole) were purchased from Pathfinder Laboratories, Inc. (St. Louis, Mo.). Benzo[a]pyrene (58.5 mCi/mmole) was purchased from Amersham (Arlington Heights, Ill.). Phenanthrene and 2-methylnaphthalene were labeled in the 9 and 10 positions, respectively. Benzo[a]pyrene was labeled in the 7 and 10 positions. Biphenyl and p-cresol were uniformly labeled

*Phanerochaete chrysosporium* was incubated at 37°–39° C. in 10 ml of the liquid culture media described by Kirk. This medium consisted of 56 mM glucose, 1.2 mM ammonium tartrate, trace elements and thiamine (1mg/l) in 20 mM dimethyl succinate buffer (pH 4.2). Cultures were established by inoculating this media with spores. For mineralization studies, $^{14}C$-labeled chemical in a minimal (<30ul) volume of acetone was added at this time.

SUMMARY

In summary, the present invention accomplishes each of the objects set forth above. The invention provides a method for degrading coal tar, coal tar distillation fractions and constituents, and cyclic and polycyclic aromatic organic compounds of the type often associated with coal tar, whether derived from coal tar or synthesized independently. This degradation takes place by means of nonspecific degradation reaction used by white rot fungi to degrade lignin.

The present invention can be used to degrade chemicals in a reaction vessel or directly in situ in the environment. In the later case it is possible to mix white rot fungi with the polluted soil and allow degradation to proceed without introducing a new danger or toxic substance to the environment.

The method of degradation disclosed provides complete degradation of organic chemicals to carbon dioxide and water. Alternatively, the reaction can be stopped at any point that desirable reaction intermediates exist. All of these benefits may be provided using only a single microorganism or group of microorganisms and no complex mixture of microorganisms is needed.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A process for degrading degradation-resistant organic pollutants comprising the steps of:
    a. combining at least one degradation-resistant organic pollutant which is an aromatic hydrocarbon having three or more fused rings selected from the group consisting of coal tar, constituents of coal tar, distillation fractions of coal tar, and polycyclic aromatic organic compounds capable of being derived from coal tar or a constituent or distillation fraction thereof, with lignin-degrading fungal enzymes expressed by *Phanerochaete chrysosporium* placed in contact with the pollutant, in the presence of hydrogen peroxide; and
    b. allowing a degradation reaction to proceed until the pollutant is converted to less toxic degradation products.

2. A process for degrading degradation-resistant organic pollutants as defined in claim 1 wherein the degradation-resistant pollutant comprises an aromatic hydrocarbon having three or more fused rings in creosote.

3. A process for degrading degradation-resistant organic pollutants as defined in claim 1 wherein the degradation-resistant pollutant comprises an aromatic hydrocarbon having three or more fused rings in anthracine oil.

4. A process for degrading degradation-resistant organic pollutants as defined in claim 1 wherein the degradation-resistant pollutant comprises benzo(a)pyrene.

5. A process for degrading degradation-resistant organic pollutants as defined in claim 1 wherein the degradation-resistant pollutant is carcinogenic.

6. A process for degrading degradation-resistant organic pollutants as defined in claim 1 wherein the degradation process occurs under aerobic conditions.

7. A process for degrading degradation-resistant organic pollutants as defined in claim 1 wherein the fungal enzymes comprise at least one lignin-degrading peroxidase.

8. A process for degrading degradation-resistant organic pollutants as defined in claim 1 wherein before step (a) the *Phanerochaete chrysosorium* has been grown in a growth medium containing a minimal nitrogen source level.

9. A process for degrading degradation-resistant organic pollutants as defined in claim 8 wherein the *Phanerochaete chrysosporium* is combined with soil containing the pollutant and such that degradation of the pollutant takes place in situ.

10. A process for degrading degradation-resistant organic pollutants as defined in claim 1 wherein nutrients are added during the degradation process.

11. A process for degrading degradation-resistant organic pollutants as defined in claim 10 wherein the nutrients comprise lignin.

12. A process for degrading degradation-resistant organic pollutants as defined in claim 10 wherein the nutrients comprise glucose.

13. A process for degrading degradation-resistant organic pollutants as defined in claim 10 wherein the nutrients comprise corn cobs.

14. A process for degrading degradation-resistant organic pollutants as defined in claim 10 wherein the nutrients comprise peas.

15. A process for degrading degradation-resistant organic pollutants as defined in claim 10 wherein the nutrients comprise straw.

16. A process for degrading degradation-resistant organic pollutants as defined in claim 10 wherein the nutrient is selected from the group consisting of saw dust and wood chips.

17. A process for degrading degradation-resistant organic pollutants as defined in claim 10 wherein nutrient comprises peanut shells.

18. A process for degrading degradation-resistant organic pollutants as defined in claim 10 wherein the nutrients are added periodically during the degradation process.

19. A process for degrading the degradation-resistant organic pollutants as defined in claim 1, further comprising the step of allowing the degradation reaction to proceed until the pollutant is converted to nontoxic degradation products comprising water and carbon dioxide.

20. A process for degrading degradation-resistant organic pollutants as defined in claim 1, wherein the hydrogen peroxide is produced by the *Phanerochaete chrysosporium*.

21. A process for degrading degradation-resistant organic pollutants as defined in claim 1, wherein the pollutant is converted to nontoxic intermediate degradation products.

22. A process for degrading degradation-resistant organic pollutants as defined in claim 21, wherein the hydrogen peroxide is produced by the *Phanerochaete chrysosporium*.

23. A process for degrading fused ring aromatic constituents of coal tar which comprises:
    a) providing a degradation resistant aromatic constituent of coal tar having three or more fused rings mixed with *Phanerochaete chrysosporium* expressing a lignin degrading peroxidase in a growth medium containing a minimal nitrogen source level under aerobic conditions; and
    b) degrading the fused ring aromatic constituent of coal tar to form less toxic degradation products.

24. A process for degrading fused ring aromatic constituents of coal tar as defined in claim 23 wherein the *Phanerochaete chrysosporium* has been grown in the growth medium prior to the *Phanerochaete chrysosporium* being mixed with the fused ring aromatic constituent of coal tar.

25. A process for degrading fused ring aromatic constituents of coal tar as defined in claim 24 wherein the growth medium includes a source of carbon, thiamine and minerals for the *Phanerochaete chrysosporium*.

26. A process for degrading fused ring aromatic constituents of coal tar as defined in claim 25 wherein the source of carbon is glucose.

27. A process for degrading fused ring aromatic constituents of coal tar as defined in claim 25 wherein the source of carbon is a carbohydrate.

28. A process for degrading fused ring aromatic constituents of coal tar as defined in claim 23 wherein the fused ring aromatic constituent of coal tar is mixed with soil from the environment and wherein the soil is mixed with the *Phanerochaete chrysosporium*.

29. A process for degrading fused ring aromatic constituents of coal tar as defined in claim 23, further comprising the step of degrading the fused ring aromatic constituent of coal tar to form nontoxic degradation products comprising water and carbon dioxide.

* * * * *

UNITED STATES PATENT AND TRADEMARK OFFICE
CERTIFICATE OF CORRECTION

PATENT NO. : 5,459,065
DATED : October 17, 1995
INVENTOR(S) : STEVEN D. AUST et al.

It is certified that error appears in the above-indentified patent and that said Letters Patent is hereby corrected as shown below:

Cover page, side 1, column 2, line 7 of text, "White Hot Fungus" should be --White Rot Fungus--

Page 2, column 2, line 13 of text, after "Kirk et al. . . . (Jul. 1976)." insert --Kirt et al., Arch. Microbiol. 117, 277-285 (1978)--

Page 2, column 2, line 21, after "Lyr, Nature (Jul. 1962)" insert --Lyr, Phytopathologische Zeitschrifte 47, No. 1, 73-83 (1963 )--

Page 2, column 2, line 6, "Environmetnal" should be --Environmental--

Column 7, line 8, adverse affect" should be --adverse effect--
Column 8, line 51, "carcinogenic compounds" should be --carcinogenic compound--
Column 10, line 58, "later case" should be --latter case--
Column 12, line 13, "wherein nutrient comprises" should be --wherein the nutrient comprises--

Signed and Sealed this

Third Day of December, 1996

Attest:

BRUCE LEHMAN

Attesting Officer       Commissioner of Patents and Trademarks